United States Patent [19]

Satake

[11] 4,403,191

[45] Sep. 6, 1983

[54] CEREAL GRAIN MOISTURE CONTENT MEASURING APPARATUS

[75] Inventor: Toshihiko Satake, Higashihiroshima, Japan

[73] Assignee: Satake Engineering Co., Ltd., Tokyo, Japan

[21] Appl. No.: 233,846

[22] Filed: Feb. 12, 1981

[30] Foreign Application Priority Data

Feb. 14, 1980 [JP] Japan .................................. 55-17362

[51] Int. Cl.³ ............................................ G01N 27/60
[52] U.S. Cl. ................................... 324/452; 324/61 R
[58] Field of Search ................ 324/65 R, 61 R, 71 R, 324/452, 457; 222/77; 177/59, 60; 73/32 A, 433

[56] References Cited

U.S. PATENT DOCUMENTS

| | | | |
|---|---|---|---|
| 1,890,545 | 12/1932 | Limbrick | 324/65 R |
| 2,625,300 | 1/1953 | Saxe | 222/77 |
| 2,665,409 | 1/1954 | Rogers | 324/61 R |
| 3,741,326 | 6/1973 | Scraper | 177/59 |

Primary Examiner—Michael J. Tokar
Assistant Examiner—Kevin O'Shea
Attorney, Agent, or Firm—Charles A. Blank

[57] ABSTRACT

A cereal grain moisture content measuring apparatus including a vessel for containing a sample of cereal grains to be measured for its moisture content formed with a discharge valve at its bottom, an electrostatic capacity sensor mounted on an inner wall surface of the vessel, a weighing device connected to the vessel and a grain feeding device mounted above the vessel. Electric circuits of the weighing device and the grain feeding device are operatively connected to an electric circuit of the sensor through a control circuit. The weighing device is adapted either to measure the weight of a predetermined volume of cereal grains, or to measure the weight of a predetermined weight of cereal grains and produce a signal to actuate a volume measuring section provided to said vessel to determine the volume of the cereal grains of the predetermined weight. The moisture content sensed by the sensor is corrected by a control circuit in terms of a predetermined density of cereal grains based on the measured weight or volume of cereal grains in the vessel.

4 Claims, 6 Drawing Figures

CEREAL GRAIN MOISTURE CONTENT MEASURING APPARATUS

BACKGROUND OF THE INVENTION

This invention relates to improvements in or relating to cereal grain moisture content measuring apparatus of the electrostatic capacity type.

Apparatus for measuring the moisture content of cereal grains of the prior art by electrostatic capacity include an electrostatic sensor built in the measuring chamber. Since the density of cereal grains in the measuring chamber may vary depending on the shape, surface coarseness and other conditions of the cereal grains, large errors have tended to occur in the values obtained in measuring the moisture content of cereal grains by means of the electrostatic sensor. Also, the apparatus of the prior art of the type described are complex in construction and mechanical and electrical failures have often occurred.

SUMMARY OF THE INVENTION

This invention has as its object the provision of an improved cereal grain moisture content measuring apparatus of the electrostatic capacity type which obviates the aforesaid disadvantages of the prior art.

To accomplish this object, the invention provides, in a cereal grain moisture content apparatus of the electrostatic capacity type, the features that a vessel mounting an electrostatic capacity sensor on its inner wall surface and provided with a discharge valve at its bottom is connected to a weighing device, that a grain feeding device is mounted above the vessel, and that electric circuits of the weighing device and grain feeding device are operatively connected to an electric circuit of the electrostatic capacity sensor.

By virtue of the aforesaid features, accurate determinations of the moisture contents of samples of cereal grains can be obtained by avoiding errors that might otherwise occur due to variations in the density of cereal grains in the vessel. A sample of cereal grains is fed by the grain feeding device into the vessel and sample feeding is interrupted when a predetermined level is reached by the cereal grains fed to the vessel to measure the density of the cereal grains and also to automatically sense the moisture content of the cereal grains so as to correct the sensed moisture content by the density of the cereal grains to avoid errors that might otherwise be caused by variations in density as described hereinabove. The apparatus has a structure which is so simple that no mechanical and electrical failures occur, and the performance of the apparatus in determing the moisture content of the sample of cereal grains is so high that grain moisture content determinations can be obtained with high accuracy at all times.

The foregoing and still other advantages of the present invention will be made more apparent from the following detailed explanation of the preferred embodiments of the invention in connection with the accompanying drawings.

DESCRIPTION OF THE PREFERRED EMBODIMENTS

Figure 1:
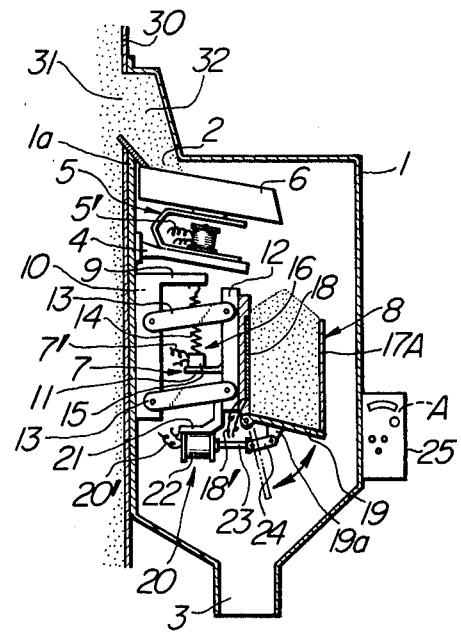
FIG. 1 is a sectional view of the cereal grain moisture measuring apparatus of the electrostatic capacity type comprising one embodiment of the invention.

In FIG. 1, the numeral 1 designates a frame of one embodiment of the cereal grain moisture content measuring apparatus in conformity with the invention formed with a grain feeding port 2 on one side of its upper portion and with a grain discharging port 3 in its lower portion. The frame 1 includes one side wall 1a having attached to an upper portion of its inner surface a fixed plate 4 mounting thereon a grain feeding device 6 comprising a grain feeding trough 6 provided with vibratory means 5. A weighing device 7 is supported on the inner surface of the side wall 1a beneath the fixed plate 4, and a vessel 8 for containing cereal grains to be measured for its moisture content is connected to one side of the weighing device 7.

The weighing device 7 comprises a support frame 10 affixed to the inner surface of the side wall 1a of the frame 1 and having an inwardly projecting suspension bar 9 formed at its upper end, a movable frame 12 located parallel to the support frame 10 as viewed vertically and having a cross bar 11 attached to its intermediate portion and projecting horizontally toward the support frame 10, and a plurality of connecting bars 13 connecting the movable frame 12 to the support frame 10 to enable the movable frame 12 to move vertically while being maintained in vertically parallel relation to the support frame 10. The suspension bar 9 is connected to the cross bar 11 by a spring scale 16 comprising a spring 14 and a weight detecting section 15.

Attached to a surface of the movable frame 12 opposite a surface thereof to which the cross bar 11 is attached is a cylindrical body 17A of the vessel 8 which is open at its top and has an electrostatic capacity sensor 18 mounted on its inner wall surface and an ON-OFF valve 19 pivotally mounted at its bottom. The ON-OFF valve 19 is adapted to be opened and closed by ON-OFF valve actuating means 20 comprising a bracket 21 attached to the lower portion of the movable frame 12, a solenoid 22 mounted on the bracket 21 and having a rod 23, and a link 24 pivotally connected at one end to the rod 23 and pivotally connected at the other end to a projection 19a on the undersurface of the ON-OFF valve 19.

The weighing device 7, vibratory means 5 and electrostatic capacity sensor 18 have electric circuits 7', 5' and 18' respectively which are operatively connected to an electric circuit 20' of the ON-OFF valve actuating device 20 through a control circuit A mounted on an outer surface of the frame 1. The numeral 25 designates an indicator mounted on a casing of the control circuit A for indicating the measured moisture content of the cereal grains in the vessel 8.

In this embodiment, the frame 1 of the cereal grain moisture content measuring apparatus is attached to a grain tank 30 as of a grain drying apparatus, and the grain feeding port 2 of the frame 1 is communicated with a grain sampling port 31 formed at the wall of the grain tank 30 through a grain flowing passage 32. Thus a sample of the cereal grains in the grain tank 30 can be fed into the vessel 8 by flowing downwardly through the grain flowing passage 32 and the grain feeding trough 6 described hereinabove.

In this embodiment, the spring scale 16 constitutes the weighing device 7. It is to be understood that the invention is not limited to this specific form of the weighing device and that any other known weighing device, such as a weighted balance, load cells, may be used.

Operation of the embodiment of the aforesaid construction will now be described. The sample of cereal grains discharged from the grain tank 30 through the grain sampling port 31 and having flowed through the grain flowing passage 32 on to the grain feeding trough 6 is fed into the vessel 8 from the lower end of the trough 6 by the action of the vibratory means 5. The cylindrical body 17A of the vessel 8 is constructed to have a predetermined volume. Thus, as the sample of cereal grains is fed into the vessel 8 in an amount commensurate with the predetermined volume of the cylindrical body 17A, the stack of the sample of grains form an angle of repose at the top and excess grains overflow the side wall of the cylindrical body 17A so that the sample of cereal grains contained in the vessel 8 may not exceed a predetermined volume at all times. At this time, the cereal grain feeding operation is interrupted by rendering the vibratory means 5 inoperative as subsequently to be described, and the weighing device 7 is actuated to measure the weight of the sample of cereal grains of the predetermined volume. At the same time, the moisture content of the sample of cereal grains of the predetermined volume is sensed by the sensor 18, and the value of the moisture content determined by the sensor 18 is corrected in terms of predetermined density based on the weight of the sample in the control circuit A. The corrected value of the moisture content of the sample is indicated by the indicator 25. Then, the ON-OFF valve 19 is brought to an open position to allow the sample of cereal grains in the vessel 8 to be discharged therefrom. The aforesaid moisture content measuring operation is repeatedly carried out in cycles with a series of samples.

Figure 3:
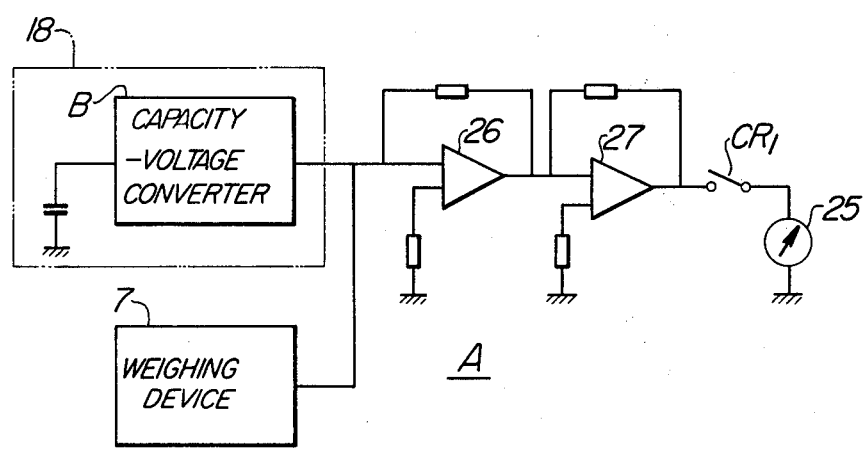
FIGS. 3 and 4 show a control circuit of the first embodiment shown in FIG. 1.
Figure 4:
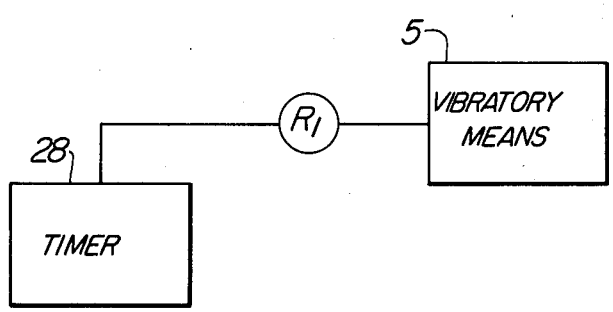

FIGS. 3 and 4 show an example of the control circuit A used in the aforesaid moisture content measuring operation. In FIG. 3, outputs of the sensor 18 comprising a power source and a C-V converter (capacity-voltage converter) B and the weighing device 7 are connected to an input of a correction circuit 26 which is connected at its output to the indicator 25 via an amplifier 27 and a relay contact $CR_1$. A relay $R_1$ may be interposed between a timer 28 and the vibratory means 5 for the grain feeding trough 6, as shown in FIG. 4. The timer 28 energizes the relay $R_1$ when the predetermined volume of the sample of cereal grains is fed into the vessel 8 and an angle of repose is formed on the stack of the sample following lapse of a predetermined grain sample feeding time as shown in FIG. 1. The relay $R_1$ opens an ON-OFF contact (not shown) mounted on the vibratory means 5 to interrupt vibration of the grain feeding trough 6, to stop the feeding of the grain sample into the vessel 8. At the same time, the relay contact $CR_1$ shown in FIG. 3 is closed to allow a current to be passed from the correction circuit 26 to the indicator 25. Thus the weighing device 7 measures the weight of the vessel 8 containing the predetermined volume of sample of cereal grains and supplies a signal to the correction circuit 26 of the control circuit A; and at the same time the sensor 18 stably senses the electrostatic capacity of the cereal grains in the vessel 8 and supplies a signal to the correction circuit 26. In the correction circuit 26, the signals from the sensor 18 and weighing device 7 are compared with each other and the measured moisture content is corrected in terms of a predetermined density based on a change in the measured weight of the sample grains by suitably increasing or decreasing the moisture content value. The corrected value of moisture content obtained in this way is amplified by the amplifier 27 and transmitted to the indicator 25 to be indicated thereby. Following completion of the moisture content measuring operation, the solenoid 22 of the actuating means 20 of the ON-OFF valve 19 is energized by a signal from the timer 28 to open the ON-OFF valve 19, to thereby permit the grain sample in the vessel 8 to be discharged therefrom. The ON-OFF valve 19 is closed when all the grain sample is discharged from the vessel 8, to allow the next following moisture content measuring operation to be carried out.

Figure 2:
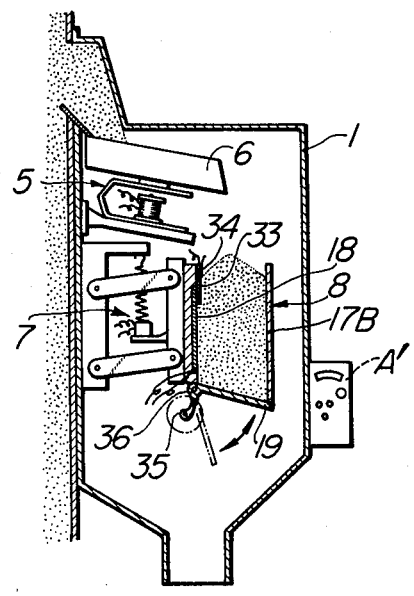
FIG. 2 is a sectional view of another embodiment of the invention.

FIG. 2 shows another embodiment of the invention. In the embodiment shown in FIG. 1, the vessel 8 is constructed to allow a sample of cereal grains of a predetermined volume to be contained therein, and the weight of the vessel 8 containing the grain sample of the predetermined volume is determined by the weighing device 7, so that the sensed moisture content of the grain sample can be corrected in terms of a predetermined density based on a change in the measured weight to make an accurate determination of the moisture content. In the embodiment shown in FIG. 2, however, the cylindrical body 17B of the vessel 8 contains a sample of cereal grains of an arbitrarily selected volume and the weighing device 7 weighs the grain sample and produces a signal when the grain sample fed into the vessel 8 has reached a predetermined value of weight. The moisture content of the grain sample of the predetermined weight is sensed by the sensor 18 in the vessel 8 and the volume of the grain sample is measured by a volume measuring section on a wall of the vessel 8 that measures the volume of the grain sample of the predetermined weight, so that the sensed moisture content can be corrected in terms of a predetermined density based on a change in volume to obtain an accurate measurement of the moisture content of the sample of cereal grains.

Elements of the embodiment shown in FIG. 2 other than the aforesaid elements and the ON-OFF valve actuating means are similar to those of the embodiment shown in FIG. 1 and their detailed description is omitted.

In FIG. 2, the volume measuring section is designated by the numeral 33 which may measure a volume based on a signal of the sensor 18 extending to a position above the grains in the vessel 8 or which may comprise a volume measuring member 34, such as a variable resistance damper, which carries out measuring of a volume. The ON-OFF valve actuating means for the ON-OFF valve 19 comprises a rotary cam 25 adapted to come into and out of engagement with a locking projection 36 formed on the ON-OFF valve 19 to thereby close or open the valve 19.

Figure 5:
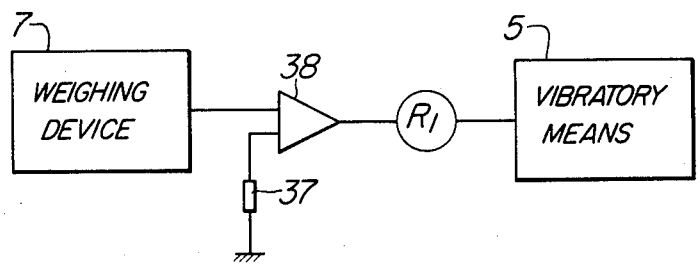
FIGS. 5 and 6 show a control circuit of the second embodiment shown in FIG. 2.
Figure 6:
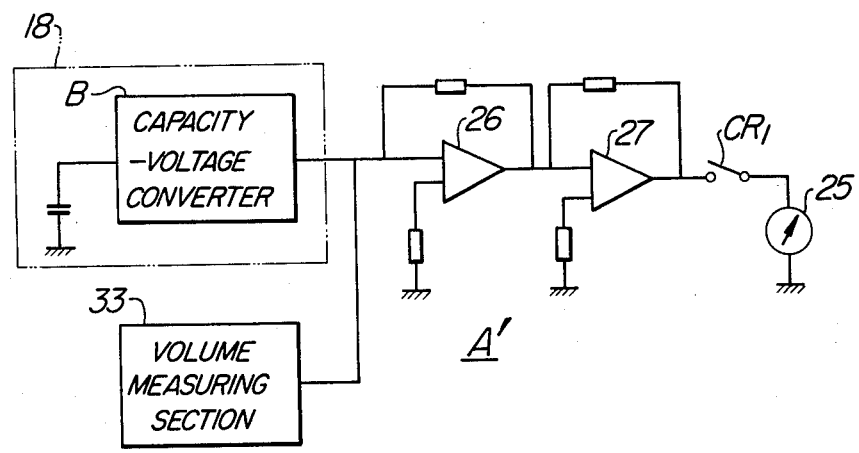

FIG. 5 shows an electric circuit of the vibratory means 5 mounted in a control circuit means A' used in performing a moisture content measuring operation by using the vessel 8 formed with the volume measuring section 33 of the embodiment shown in FIG. 2. The weighing device 7 and a setter 37 is connected to an input of a comparator 38 connected at its output to the vibratory means 5 via the relay $R_1$. A signal from the weighing device 7 and an output of the setter 37 which is set at an arbitarily selected weight of cereal grains are supplied to the comparator 38 and compared with each other. When the two signals coincide with each other, the comparator 38 issues a coincidence signal which energizes the relay R₁ for opening an ON-OFF contact (not shown) mounted in the vibratory means 5, to thereby interrupt vibration of the trough 6 and stop feeding of the sample of cereal grains. At the same time, the contact CR₁ shown in FIG. 6 is closed and allows a current to be passed from the correction circuit 26 and indicator 25. In this case, the electric circuit is connected to the volume measuring section 33 which is used in place of the weighing device 7 shown in FIG. 3, so that the circuit operates in the same manner as the circuit shown in FIG. 3 and enables the volume of the cereal grains of a predetermined weight to be measured in a stable condition and permits the sensed moisture content to be corrected in terms of a predetermined density based on a change in volume. The corrected moisture content can be indicated by the indicator 25.

In the embodiment shown and described hereinabove, the weight of the sample of cereal grains flowing downwardly from the grain feeding trough 6 into the vessel 8 is measured by the weighing device 7 which issues a signal when the measured weight of the sample reaches a predetermined value to interrupt operation of the vibratory means 5 and stop feeding of the grain sample through the grain feeding trough 6. The moisture content of the grain sample in the cylindrical body 17B is sensed by the electrostatic capacity sensor 18 and the volume thereof is measured by the volume measuring section 33. The sensor 18 and volume measuring section 33 each issue a signal supplied to the control circuit A', and the sensed moisture content is corrected in terms of a predetermined density to thereby obtain a corrected, accurate moisture content which is indicated by the indicator 25.

From the foregoing description, it will be appreciated that in the cereal grain moisture content measuring apparatus according to the invention, a vessel having a sensor on its inner wall surface and formed with a discharge valve at its bottom is connected to a weighing device; a cereal grain feeding device is mounted above the vessel; and electric circuits of the weighing device and cereal grain feeding device are operatively connected to an electric circuit of the sensor. A sample of cereal grains flowing downwardly from the cereal grain feeding device is supplied to the vessel, and the weight or volume of the sample of cereal grains in the vessel is measured and the moisture content thereof is sensed by the sensor after the cereal grain feeding is interrupted. The sensed moisture content is corrected in terms of a predetermined density based on a change in weight or volume, so that an accurate moisture content of the sample of cereal grains can be determined. The disadvantage of the prior art that the sensed moisture contents have often been erroneous due to variations in the density of grains can be eliminated, and the accurate value can be readily indicated. Moreover, the apparatus is of simple construction and free from mechanical and electrical failures and has improved performance. Thus the apparatus according to the invention is of great use in enabling cereal grains of high quality having a predetermined moisture content to be positively obtained on mass production basis in a smooth operation.

What is claimed is:

1. A cereal grain moisture content measuring apparatus comprising: a vibratory feeding trough through which cereal grains are laterally advanced to finally freely drop from one end thereof, a measuring vessel located beneath said feeding trough and provided with a sensor mounted on an inside wall surface of said vessel and connected to an electrostatic capacity measuring circuit and with a bottom wall capable of opening and closing, a weighing mechanism connected to said vessel and including a weight measuring circuit, and a control circuit connected to said electrostatic capacity measuring circuit and said weight measuring circuit for correcting the value of electrostatic capacity measured at said vessel by the weight of the grains measured by the weighing mechanism, whereby the moisture content of cereal grains filled to overflow said vessel in a spill flow manner is measured.

2. A cereal grain moisture content measuring apparatus as claimed in claim 1, wherein said weighing mechanism connected to said vessel measures the weight of cereal grains in the vessel containing a predetermined volume of cereal grains.

3. A cereal grain moisture content measuring apparatus as claimed in claim 1, wherein said vibratory feeding trough is provided with an electric circuit including a timer.

4. A cereal grain moisture content measuring apparatus as claimed in claim 3, wherein said electric circuit of said feeding trough is connected to said circuit of said weighing device through a relay.

* * * * *